United States Patent [19]

Millauer

[11] Patent Number: 5,527,967

[45] Date of Patent: Jun. 18, 1996

[54] PROCESS FOR PREPARING TERTIARY DIARYLALKYLPHOSPHINES

[75] Inventor: Hans Millauer, Eschborn, Germany

[73] Assignee: Hoechst Aktiengesellschaft, Frankfurt am Main, Germany

[21] Appl. No.: 449,309

[22] Filed: May 24, 1995

[30] Foreign Application Priority Data

May 26, 1994 [DE] Germany .......................... 44 18 346.1

[51] Int. Cl.$^6$ ...................................................... C07F 9/02
[52] U.S. Cl. ............................................................. 568/17
[58] Field of Search .................................................. 568/17

[56] References Cited

U.S. PATENT DOCUMENTS

| | | | |
|---|---|---|---|
| 2,902,517 | 9/1959 | Schmerling | 260/606.5 |
| 2,912,465 | 11/1959 | Ranisden | 260/606.5 |
| 3,751,481 | 8/1973 | Weinberg | 260/601.5 P |
| 4,507,501 | 3/1985 | Nelson | 568/17 |
| 4,618,720 | 10/1986 | Bay et al. | 568/17 |
| 4,668,823 | 5/1987 | Murray | 568/17 |
| 4,758,315 | 7/1988 | Folest et al. | 204/59 R |
| 5,288,912 | 2/1994 | Devon | 568/17 |

FOREIGN PATENT DOCUMENTS 0196742  10/1986  European Pat. Off. .

OTHER PUBLICATIONS

European Search Report No. 95107514.2, Aug. 31, 1995.

*Primary Examiner*—Porfirio Nazario-Gonzales
*Attorney, Agent, or Firm*—Connolly and Hutz

[57] ABSTRACT

The invention relates to a process for preparing phosphines

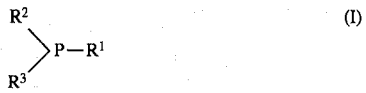

where, for example $R^1$ is $(C_1$–$C_{10})$alkyl, $(C_3$–$C_{10})$cycloalkyl, C(YZ)aryl Y, Z is $(C_1$–$C_4)$alkyl, hydrogen, Aryl is phenyl, naphthyl, anthracenyl, phenanthrenyl, or biphenyl, binaphthyl and $R^2$, $R^3$ are, independently of one another, phenyl, naphthyl or anthracenyl, by reacting a diarylphosphine

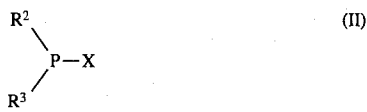

where X is bromine, chlorine, fluorine, $(C_1$–$C_4)$alkoxy, O-phenyl, with a reducing agent and a quaternary ammonium compound

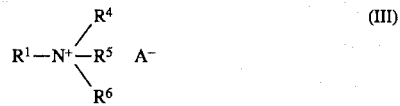

where A is an anion of an organic or inorganic acid.

18 Claims, No Drawings

PROCESS FOR PREPARING TERTIARY DIARYLALKYLPHOSPHINES

DESCRIPTION

The invention relates to a process for preparing tertiary diarylalkylphosphines by reductive coupling of halodiarylphosphines with a quaternary ammonium compound, the reduction preferably proceeding via an electrochemical process.

Tertiary phosphines, in particular tertiary phosphines having bulky aromatic or araliphatic ligands, are used in a great variety of forms as ligands for complexing heavy metal atoms. The complexes thus obtained have achieved great importance as catalysts in a series of important industrial processes, e.g. hydrogenations and oxosyntheses.

Tertiary diarylalkylphosphines can in principle be prepared by two different methods, generally starting from industrially available diarylphosphorus(III) compounds such as, for example, diarylchlorophosphines and forming a third P-C bond.

"Methoden der organischen Chemie" (Houben-Weyl), 4th edition (1963), volume XII/1, page 32 ff describes a frequently used, general method which comprises reacting a suitable organometallic compound such as a Grignard compound or an organic lithium compound with diarylchlorophosphines, for example:

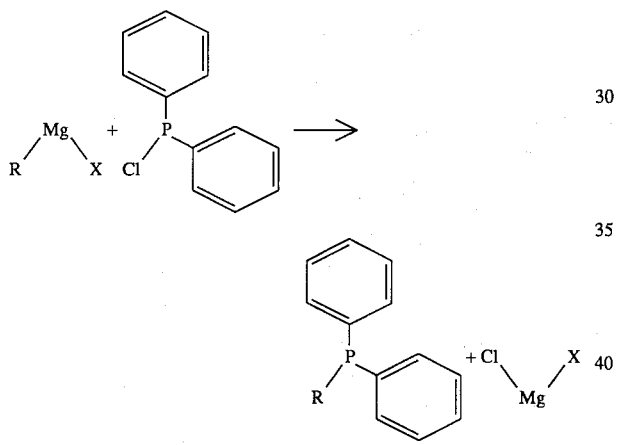

R = Alkyl, Aralkyl;   X = Cl, Br

This method has the disadvantage that the corresponding organometallic compounds are in some cases impossible or difficult to obtain, particularly when certain substituents, such as keto groups or ester groups, are still present on the radical R. It has also been observed that the organometallic intermediate, instead of forming the intended carbon-phosphorus bond, forms other products which result from, for example, coupling or ring-closure reactions. A further, general difficulty in these processes is that in such organometallic processes it is typically necessary to use hydrocarbons or ethers having low flash points and ignition temperatures, which makes industrial production difficult.

A second known method comprises producing the metal salt of a diarylphosphine anion and reacting this with an alkyl halide. However, this process cannot be generally used:

T. J. Hall and J. H. Hargis, J. Org. Chem. 51, 4185 ff (1986) describe the electrochemical reduction of halodiarylphosphines, obtaining tetraphenyldiphosphine as the sole product. When an attempt was made to trap the diphenylphosphine anion postulated as intermediate in situ using benzyl bromide, no benzyldiphenylphosphine was able to be detected.

The European Patent EP 0 268 526 describes an electrochemical process for preparing tertiary diarylalkylphosphines, wherein the electrochemical reduction of arylhalophosphines is carried out in the presence of organic aliphatic halides in an electrolysis cell equipped with electrodes in an organic solvent medium containing an inert electrolyte and a consumable anode is used. This process gives satisfactory to good yields in the case of alkyl halides having pure alkyl radicals, e.g. n-butyl radicals, or even certain substituted alkyl radicals, but on the other hand moderate to poor yields in the case of araliphatic radicals (30% or 44% for benzyl chloride).

There was thus a great need for a process which allows the linking of a diarylphosphinyl radical with araliphatic radicals to give tertiary diarylalkylphosphines to be carried out in high yields in a technically simple and safe manner.

This object is achieved by a process for preparing phosphines of the formula (I)

where:

$R^1$ is $(C_1-C_{10})$ alkyl, $(C_3-C_{10})$ cycloalkyl, C (YZ) aryl

Y, Z is $(C_1-C_4)$alkyl, hydrogen,

Aryl is phenyl, naphthyl, anthracenyl, phenanthrenyl or biphenyl, binaphthyl where the alkyl and cycloalkyl radicals can also be substituted by CN, $O(C_1-C_4)$ alkyl, $CO(C_1-C_4)$ alkyl, COO $(C_1-C_4)$ alkyl, $-CH_2-CH_2-(C_1-C_{10})$ polyfluoroalkyl, where the cycloalkyl radicals can also contain —O or —S-moieties in the ring;

the aryl radicals can be substituted by CN, halogen, CO $(C_1-C_4)$ alkyl, $COO(C_1-C_4)$ alkyl, $-CH_2-CH_2-(C_1-C_{10})$ polyfluoroalkyl, a

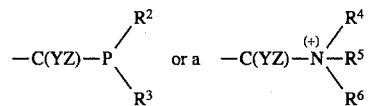

radical, $R^2$, $R^3$ are, independently of one another, phenyl, naphthyl, anthracenyl, which can also be substituted by halogen, $(C_1-C_4)$alkyl, $(C_1-C_4)$alkoxy, $R^4$, $R^5$, $R^6$ are identical or different and are $(C_1-C_{12})$alkyl or $R^4$ and $R^5$ together form a 5-membered or 6-membered ring which can, if desired, contain further N, O or S atoms in the ring, or $R^4$, $R^5$ and $R^6$ form a bicyclic ring system having nitrogen as bridge head atom and, if desired, further nitrogen, oxygen or sulphur atoms in the ring, which comprises reacting a diarylphosphine of the formula

where $R^2$ and $R^3$ are as defined above and

X is bromine, chlorine, fluorine, $(C_1-C_4)$ alkoxy, O-phenyl, with a reducing agent and a quaternary ammonium compound of the formula (III)

where
R¹, R⁴, R⁵, R⁶ are as defined above and
A is an anion of an organic or inorganic acid.

The process is of great importance for preparing compounds of the formula (I) where R¹ is $(C_1-C_8)$alkyl, $(C_3-C_8)$cycloalkyl, $CH_2$-phenyl, $—CH_2$-naphthyl or $CH_2$-biphenyl, where the phenyl, biphenyl and naphthyl radicals can be substituted by

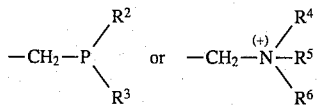

and R², R³ are phenyl or naphthyl, R⁴, R⁵, R⁶ are $(C_1-C_{10})$alkyl and X is bromine, chlorine or fluorine.

The process is also important for preparing the following compounds of the formula (I)

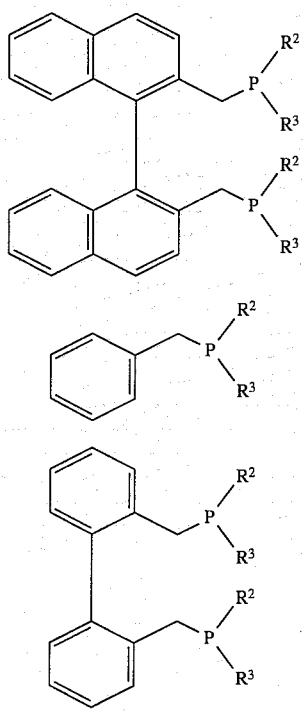

The compounds of the formula (III) can be quaternary ammonium compounds having 4 identical radicals. If the starting compound has different radicals R¹, R⁴, R⁵, R⁶, the radical R¹ to be transferred has to preferentially bond to the diphenylphosphine group. Examples which may be mentioned of the first group are: tetramethylammonium, tetraethylammonium, tetrapropylammonium or tetrabutylammonium salts. Examples of the second group which may be mentioned are (R¹ is always the first-named group): allyltrimethylammonium, benzyltrimethylammonium, N-benzyl-N-methylpiperidinium, N-benzyl-N,N'-dimethylpiperazinium, N-benzyl-N-methylmorpholinium, N-benzyl (diazabicyclo [2.2.2]octyl) ammonium, (2 -naphthylmethyl) triethylammonium, 4 - fluorobenzyltrimethylammonium, pentafluorobenzyltrimethylammonium, 2,6-dichlorobenzyltrimethylammonium, 2-cyanobenzyltrimethylammonium, 4-(trifluoromethyl)benzylammonium, cyclohexyltrimethylammonium or (carbomethoxymethyl)trimethylammonium salts.

Bisquaternary ammonium compounds (bisquats), for example, 2,2'-bis[(trimethylammonio) methyl]biphenyl salts or 2,2'-bis [(trimethylammonio) methyl]-1,1'-binaphthyl salts can likewise be used as starting compounds of the formula (III).

Of interest here are, for example, the compounds where formula (III) is

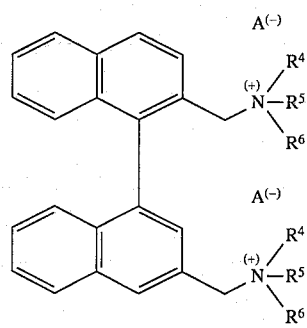

where R⁴, R⁵, R⁶ and A are as defined above.

When carrying out the process, the reduction of the compounds of the formula (II) can be carried out in the presence of the ammonium compound of the formula (III), but it is also possible to carry out the reduction first and subsequently add the ammonium compound.

The reduction of the diarylphosphines of the formula (II) is preferably carried out electrochemically, but can also be carried out by a chemical route, e.g. using metals, in particular alkali metals ("Methoden der organischen Chemie" (Houben Weyl), 4th edition (1963), volume XII/1, page 56).

However, in comparison with the electrochemical reduction, this procedure has the disadvantage that again the work methods of organometallic synthesis, which are complicated in terms of safety, would have to be used. In the electrochemical process, in contrast, the reduction step is carried out starting with cheap, safe to handle, industrially available starting materials in a very simple and technically controllable way.

Use is made of an undivided electrolysis cell which can be of any shape, for example a trough-shaped cell or a flow-through cell, and which has at least one cathode and one anode. The cathode comprises one of the usual metals, for example aluminum, magnesium, iron, nickel, chromium, titanium, copper, zinc, lead, cadmium, silver, gold or platinum or alloys of these metals, preferably chromium-nickel steel, or carbon materials, for example graphite or vitreous carbons.

As anode, use is made of metals which are difficult to deposit cathodically under the electrolysis conditions, for example aluminum, calcium or preferably magnesium.

Suitable electrolytes are aprotic, dipolar solvents, for example acetonitrile, dimethylacetamide, N-methylpyrrolidone, tetrahydrofuran or preferably dimethylformamide. If the addition of the quaternary ammonium compound is carried out only after electrolysis, an inert conductance salt which is soluble in the electrolyte can be additionally added to improve the electric conductivity, for example alkali metal or alkaline earth metal halides, for example sodium bromide or preferably magnesium chloride.

The process of the invention is carried out at temperatures between about 0° C. and 80° C., preferably between 10° C. and 60° C.

The electrolysis is carried out at current densities between about 1 and 100 mA/cm², preferably between 5 and 50 mA/cm².

During the electrolysis, the electrolyte is advantageously moved relative to the electrodes by stirring or flow. If the reaction is carried out with the quaternary ammonium compound being added during the electrochemical reduction, the electrolyte can be stirred further for a certain time subsequent to the electrolysis to complete the conversion.

The isolation of the process products is carried out in a manner known per se, for example by distilling off the solvent, dissolving the residue in a further water-immiscible solvent selected from the group consisting of hydrocarbons, halogenated hydrocarbons, ethers or ketones, extracting said solution with dilute mineral acid, evaporating the solvent and isolating the crude product obtained as residue by fractional distillation or crystallization.

The following examples serve to illustrate the invention without limiting it to them.

The compounds of the formula (III) can be prepared by generally known methods, e.g. by reacting an alkyl halide with a tertiary amine ("Methoden der organischen Chemie" (Houben-Weyl), 4th edition (1963), volume XI/2, page 593 ff.).

2,2,-bis[(trimethylammonium)methyl]-1,1'-binaphthyl dibromide can be prepared, for example, in virtually quantitative yield by reacting 2,2'-bis(bromomethyl)-1,1'-binaphthyl with trimethylamine in dimethylformamide at 70° C.

EXAMPLE 1

An undivided electrolysis cell is used. The cell comprises a cylindrical glass vessel (diameter 40 mm; height 110 mm) fitted with a cooling jacket and a glass lid provided with a ground glass joint, in which lid there are located 5 smaller ground openings. The anode used is a magnesium rod (diameter 10 mm; length 100 mm; immersion depth about 55 mm), the cathode is a rectangular mesh of chromium-nickel steel (60×500 mm) which is shaped into a cylinder and is arranged concentrically around the anode (the spacing between the electrodes is about 3 mm). The electrodes are held in the lid of the cell by stiff wires of chromium-nickel steel which serve as power leads. The cell is further equipped with a thermometer, a gas inlet tube for nitrogen and a bubble counter. A further opening is closed by a septum of silicone rubber. The electrolyte is stirred by means of a magnetic bar.

The dry cell is charged with 60 ml of dimethylformamide (max. 0.1% of water) and 10.51 g (0.050 mol) of tetraethylammoniumbromide. While stirring, a dry stream of nitrogen is passed through the mixture for 0.5 h, 8.82 g (0.040 mol) of chlorodiphenylphosphine are subsequently added and the electrolysis is commenced immediately afterwards with continued stirring and a passing through of a slow stream of nitrogen. The current is a constant 0.3 A, the temperature is from 35° to 40° C. The cell voltage is in the range from 0 to 1.5 volts. The amount of charge is 1.41 Ah. After electrolysis, the electrolyte is stirred for a further 6 h at 50° C. According to analysis by gas chromatography (internal standard: 2-methylnaphthalene) the electrolyte contains 5.15 g of ethyldiphenylphosphine; this corresponds to a yield of 60% based on chlorodiphenylphosphine used. The product is isolated in the following way: The electrolyte is evaporated on a rotary evaporator at 70° C./20 mbar, the residue obtained is taken up in 150 ml of 1N hydrochloric acid and 50 ml of methylene chloride and stirred thoroughly; the methylene chloride phase is washed with 150 ml of water, dried over sodium sulphate and the methylene chloride is distilled off. Fractional distillation of the residue using a 10 cm Vigreux column under reduced pressure gives, at bp. 110° C./0.01 mbar, a fraction having a purity of 97.5%. The $^{31}$P NMR spectrum and the $^1$H NMR spectrum agree with an authentic sample.

EXAMPLE 2

An electrolysis cell as described in Example 1 is used. The electrolyte comprises 60 ml of dimethylformamide (max. 0.1% of water), 16.12 g (0.050 mol) of tetra-n-butylammonium bromide and 8.82 g (0.040 mol) of chlorodiphenylphosphine. The electrolysis is carried out as described in Example 1. After the electrolysis, the electrolyte is stirred for a further 2 h at 35°–40° C. According to analysis by gas chromatography (internal standard: 2-methylnaphthalene), the electrolyte contains 6.96 g of n-butyldiphenylphosphine; this corresponds to a yield of 72% based on chlorodiphenylphosphine used. Workup and fractional distillation as described in Example 1 gives 4.78 g of 94%-pure product. The $^{31}$P NMR spectrum and the $^1$H NMR spectrum agree with an authentic sample.

EXAMPLE 3

An electrolysis cell as described in Example 1 is used. The electrolyte comprises 50 ml of dimethylformamide (max. 0.1% of water), 8.16 g (0,030 mol) of benzyltriethylammonium bromide and 5.52 g (0.025 mol) of chlorodiphenylphosphine. The amount of charge is 1.08 Ah. The electrolysis and workup of the electrolyte are carried out as described in Example 1. After evaporating the methylene chloride phase, there remain 6.60 g of residue which, according to analysis by gas chromatography (internal standard: 2-methylnaphthalene), contains 85% by weight of benzyldiphenylphosphine. The material yield based on chlorodiphenylphosphine used is 81%. Fractional distillation gives a 95%-pure product whose $^{31}$P NMR spectrum agrees with an authentic sample.

EXAMPLE 4

An electrolysis cell as described in Example 1 is used. The electrolyte comprises 50 ml of dimethylacetamide (max. 0.1% of water), 4.70 g (0,025 mol) of benzyltrimethylammonium chloride and 6.62 g (0,030 mol) of chlorodiphenylphosphine. The amount of charge is 0.96 Ah. The electrolysis is carried out at a current of 0.3 A and a temperature of 25° C. The electrolyte is subsequently stirred for a further 3 h at 35°–40° C. According to analysis by gas chromatography (internal standard 2-methylnaphthalene), the electrolyte contains 5.47 g of benzyldiphenylphosphine in dissolved form, which can be isolated by workup as described in Example 1. The yield is 79% based on benzyltrimethylammonium chloride used.

EXAMPLE 5

An electrolysis cell as described in Example 1 is used. The electrolyte comprises 50 ml of dimethylformamide (max. 0.1% of water) and 5.57 g (0,030 mol) of benzyltrimethylammoniumchloride. A total of 8.82 g (0.040 mol) of chlorodiphenylphosphine are added during the electrolysis in 4 equal portions: 2.2 g at the beginning of the electrolysis, 2.2 g after 0.32 Ah, 2.2 g after 0.64 Ah and 2.2 g after 1.34 Ah. The electrolysis is carried out with continued stirring and passage of a slow stream of nitrogen and a current of 0.3 A and a temperature of from 20° to 25° C. After an amount of charge of 1.61 Ah, the electrolyte contains, according to analysis by gas chromatography (internal standard: 2-methylnaphthalene) 7.10 g of benzyldiphenylphosphine which can be isolated by workup as described in Example 1. The yield is 85% based on benzyltrimethylammonium chloride used.

EXAMPLE 6

An electrolysis cell as described in Example 1 is used. The electrolyte comprises 70 ml of dimethylformamide (max. 0.1% of water), 0.4 g of anhydrous magnesium chloride and 6.62 g (0.030 mol) of chlorodiphenylphosphine. The electrolysis is carried out as described in Example 1. The electrolysis temperature is 25° C. After an amount of charge of 0.96 Ah, the electrolysis is ended. 4.64 g (0.025 mol) of benzyltrimethylammonium chloride are then introduced into the electrolyte with exclusion of air and the mixture is stirred at 35° C. After 3 h the reaction mixture contains, according to analysis by gas chromatography (internal standard: 2-methylnaphthalene), 5.72 g of benzyldiphenylphosphine (yield 83%, based on benzyltrimethylammonium chloride used) which can be isolated by workup as described in Example 1.

EXAMPLE 7

An electrolysis cell as described in Example 1 is used. The electrolyte comprises 50 ml of dimethylformamide (max. 0.1% of water), 0.4 g of anhydrous magnesium chloride and 6.62 g (0.030 mol) of chlorodiphenylphosphine. The electrolysis is carried out as described in Example 1. The electrolysis temperature is 25° C. After an amount of charge of 1.0 Ah, the electrolysis is ended. 5.58 g (0,010 mol) of 2,2'-bis[(trimethylammonio)methyl]-1,1'-binaphthyl dibromide are then introduced into the electrolyte under nitrogen and the mixture is stirred for 3 h at from 30° to 35° C. until a clear solution is formed. The workup is carried out as follows with exclusion of atmospheric oxygen: The electrolyte is evaporated on a rotary evaporator at 70° C./20 mbar, the residue obtained is taken up in 100 ml of 1N hydrochloric acid and 50 ml of methylene chloride and stirred thoroughly. The methylene chloride phase is washed with 100 ml of water, dried over sodium sulphate and the methylene chloride is evaporated under reduced pressure. The residue comprises 8.20 g of resinous solid. This residue is refluxed for about 1 h with 50 ml of isopropanol while stirring vigorously. In this way, the compact solid forms a finely divided, colorless product. After cooling to room temperature, this product is filtered off with suction, washed 3× with 10 ml each time of cold isopropanol and is dried in a stream of nitrogen. This gives 5.45 g of 2,2'-bis[(diphenylphosphino)methyl]-1,1'-binaphthyl ("naphos"). The yield is 84% based on 2,2'-bis[(trimethylammonio)methyl]-1,1'-binaphthyl dibromide used. $^{31}$P NMR spectrum (CDCl$_3$): The signal at −12.3 ppm corresponds to 96% of the total phosphorus. The $^1$H NMR spectrum is identical with an authentic sample.

EXAMPLE 8

The procedure of Example 7 is repeated, but using an electrolyte comprising 5.58 g (0.010 mol) of 2,2'-bis[(trimethylammonio)methyl]-1,1'-binaphthyl dibromide, 6.62 g (0.030 mol) of chlorodiphenylphosphine and 50 ml of dimethyl formamide (max. 0.1% of water) in the electrolysis. The amount of charge is 0.96 Ah. Workup gives 5.1 g of 2,2'-bis[(diphenylphosphino)methyl]-1,1'-binaphthyl ("naphos"). This corresponds to a yield of 78% based on 2,2'-bis[(trimethylammonio)methyl]-1,1'-binaphthyl dibromide used.

EXAMPLE 9

A dry 100 ml round-bottomed flask, which is equipped with a magnetic stirrer bar, nitrogen inlet tube, bubble counter and a septum and has previously been flushed with dry nitrogen, is charged with 1.86 g (0.010 mol) of powdered benzyltrimethylammonium chloride and, by means of a syringe via the septum, 20 ml of a solution of 2.24 g (0.010 mol) of potassium diphenylphosphide in tetrahydrofuran (obtained as a ready-prepared 0.5M solution from Aldrich-Chemie GmbH & Co. KG, D-89555 Steinheim, Germany) at room temperature in one shot. The mixture is stirred for a further 4 hours at room temperature, with the color gradually changing from red to yellow. With exclusion of atmospheric oxygen, the reaction mixture is mixed by stirring with 20 ml of 1N hydrochloric acid, the tetrahydrofuran phase is separated off, the aqueous phase is extracted twice with 10 ml of tetrahydrofuran and the two extracts are combined with the tetrahydrofuran phase. According to analysis by gas chromatography (internal standard: 2-methylnaphthalene), the combined tetrahydrofuran phases contained 2.50 g of benzyldiphenylphosphine; this corresponds to a yield of 90%.

EXAMPLE 10

An apparatus as described in Example 9 is used. After making inert with nitrogen, it is charged with 5.58 g (0.010 mol) of 2,2'-bis[(trimethylammonio)methyl]1,1'-binaphthyl dibromide and 44 ml of a solution of 4.93 g (0.022 mol) of potassium diphenylphosphide in tetrahydrofuran (as 0.5 M solution obtained ready-made from Aldrich-Chemie GmbH a Co, KG, D-89555 Steinheim, Germany) were added thereto while stirring over a period of about 5 minutes by means of a syringe. The temperature is from 20° to 30° C. The reaction mixture is stirred for a further 3 h at room temperature and is then mixed with 20 ml of 1N hydrochloric acid, the tetrahydrofuran phase is separated off and the aqueous phase is extracted twice with 10 ml of tetrahydrofuran. The combined tetrahydrofuran phases are concentrated by distillation under reduced pressure. The residue is admixed with 50 ml of isopropanol and heated under reflux for i hour while stirring vigorously, the resinous material being converted into a colorless crystalline product. After cooling to room temperature, the product is filtered off with suction, washed 3× with 10 ml each time of cold isopropanol and dried in a stream of nitrogen. This gives 5.4 g of 2,2'-bis[(diphenylphosphino)methyl]-1,1'-binaphthyl ("naphos"). The yield is 83% based on the 2,2'-bis[(trimethylammonio)methyl]-1,1'-binaphthyl dibromide used.

I claim:

1. A process for preparing phosphines of the formula (I)

wherein:

R$^1$ is (C$_1$–C$_{10}$)alkyl, (C$_3$–C$_{10}$)cycloalkyl, C(YZ)aryl

Y, Z is (C$_1$–C$_4$)alkyl, hydrogen,

Aryl is phenyl, naphthyl, anthracenyl, phenanthrenyl or biphenyl, binaphthyl where the alkyl and cycloalkyl radicals are optionally substituted by CN, O(C$_1$–C$_4$) alkyl, CO (C$_1$–C$_4$)alkyl, COO(C$_1$–C$_4$)alkyl, —CH$_2$—CH$_2$— (C$_1$–C$_{10}$)polyfluoroalkyl, where the cycloalkyl radicals optionally contain —O- or —S-moieties in the ring;

the aryl radicals are optionally substituted by CN, halogen, CO (C$_1$–C$_4$) alkyl, COO(C$_1$–C$_4$) alkyl, —CH$_2$—CH$_2$—(C$_1$-C$_{10}$)- polyfluoroalkyl, a

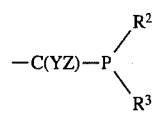

or a

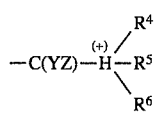

radical,

R$^2$, R$^3$ are, independently of one another, phenyl, naphthyl, anthracenyl, which are optionally substituted by halogen, (C$_1$-C$_4$)alkyl, (C$_1$-C$_4$)alkoxy, R$^4$, R$^5$, R$^6$ are identical or different and are (C$_1$-C$_{12}$)alkyl or R$^4$ and R$^5$ together form a 5-membered or 6-membered ring which can optionally contain further N, O or S atoms in the ring, or R$^4$, R$^5$ and R$^6$ form a bicyclic ring system having nitrogen as bridge head atom and optionally further nitrogen, oxygen or sulphur atoms in the ring, which comprises reacting a diarylphosphine of the formula (II)

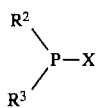

wherein R$^2$ and R$^3$ are as defined above and

X is bromine, chlorine, fluorine, (C$_1$-C$_4$)alkoxy, O-phenyl, with a reducing agent and a quaternary ammonium compound of the formula (III)

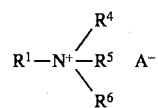

where

R$^1$, R$^4$, R$^5$, R$^6$ are as defined above and

A is an anion of an organic or inorganic acid.

2. The process as claimed in claim 1, wherein in formula (I)

R$^1$ is (C$_3$-C$_8$) alkyl, (C$_3$-C$_8$) cycloalkyl, CH$_2$-phenyl, —CH$_2$-naphthyl, CH$_2$-biphenyl, where the phenyl, biphenyl and naphthyl radicals are optionally substituted by

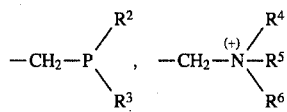

R$^2$, R$^3$ are phenyl and naphthyl,

R$^4$, R$^5$, R$^6$ are (C$_1$-C$_{10}$) alkyl and

X is bromine, chlorine or fluorine.

3. The process as claimed in claim 1, wherein the formula (I) is

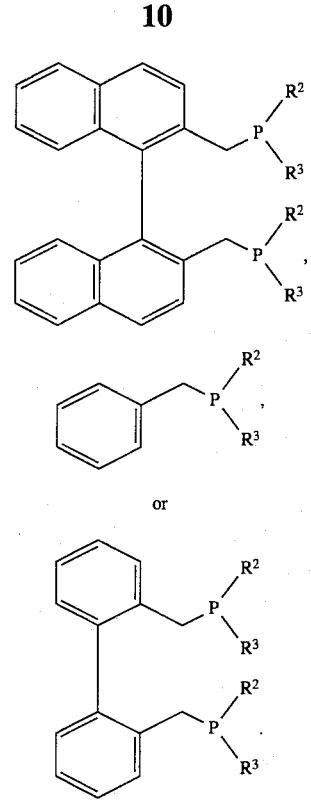

4. The process as claimed in claim 1, wherein the compound of the formula (III) is a tetramethylammonium, tetraethylammonium, tetrapropylammonium, tetrabutylammonium, allyltrimethylammonium, benzyltrimethylammonium, N-benzyl -N-methylpiperidinium, N-benzyl-N,N'-dimethylpiperazinium, N-benzyl-N-methylmorpholinium, N-benzyl-(diazobicyclo[2.2.2]octyl)ammonium, (2-naphthylmethyl)triethylammonium, 4- fluorobenzyltrimethylammonium, pentafluorobenzyltrimethylammonium, dichlorobenzyltrimethylammonium, 2-cyanobenzyltrimethylammonium, 4-(trifluoromethyl)benzylammonium, cyclohexyltrimethylammonium, (carbomethoxymethyl)trimethylammonium, 2,2'-bis[(trimethylammonio)methyl]biphenyl or 2,2'-bis[(trimethylammonio)methyl]-1,1'-binaphthyl salt.

5. A process as claimed in claim 1, wherein the formula (III) is

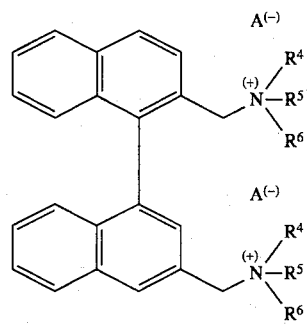

where

R$^4$, R$^5$, R$^6$ are identical or different and are (C$_1$-C$_{12}$)alkyl or R$^4$ and R$^5$ together form a 5-membered or 6-membered ring which can optionally contain further N, O or S atoms in the ring, or $R^4$, $R^5$ and $R^6$ form a bicyclic ring system having nitrogen as bridge head atom and optionally further nitrogen, oxygen or sulphur atoms in the ring, and A is an anion of an organic or inorganic acid.

6. The process as claimed in claim 1, wherein the ammonium compound of the formula (III) is added prior to the reduction.

7. The process as claimed in claim 1, wherein the ammonium compound of the formula (III) is added after the reduction.

8. The process as claimed in claim 1, wherein the reduction is carried out using metals or metal hydrides.

9. The process as claimed in claim 1, wherein the reduction is carried out electrochemically.

10. The process as claimed in claim 9, wherein the electrochemical reduction is carried out in an undivided electrolysis cell.

11. The process as claimed in claim 9, wherein the cathode comprises aluminum, magnesium, iron, nickel, chromium, titanium, copper, zinc, lead, cadmium, silver, gold, platinum or an alloy of these metals.

12. The process as claimed in claim 9, wherein the cathode comprises graphite or vitreous carbon.

13. The process as claimed in claim 9, wherein the anode used is aluminum, calcium or magnesium.

14. The process as claimed-in claim 9, wherein the electrolyte used is a dipolar aprotic solvent.

15. The process as claimed in claim 9, wherein the reaction is carried out at temperatures between 0° and 80° C.

16. The process as claimed in claim 9, wherein the electrolysis is carried out at current densities between 1 and 100 mA/cm$^2$.

17. The process as claimed in claim 1, wherein the solvent used is diethyl ether, diisopropyl ether, di-n-propyl ether, methyl t-butyl ether or tetrahydrofuran.

18. The process as claimed in claim 9, wherein the electrolyte used is acetonitrile, dimethylacetamide, N-methylpyrrolidone, tetrahydrofuran, or dimethylformamide.

* * * * *

UNITED STATES PATENT AND TRADEMARK OFFICE
CERTIFICATE OF CORRECTION

PATENT NO. : 5,527,967
DATED : June 18, 1996
INVENTOR(S) : Hans Millauer

It is certified that error appears in the above-indentified patent and that said Letters Patent is hereby corrected as shown below:

In Claim 2, column 9, line 51, "$(C_3-C_8)$ alkyl" should be -- $(C_1-C_8)$ alkyl--.

Signed and Sealed this

Eighth Day of October, 1996

Attest:

BRUCE LEHMAN

*Attesting Officer*     *Commissioner of Patents and Trademarks*